United States Patent [19]

Knebel et al.

[11] Patent Number: 4,931,594

[45] Date of Patent: Jun. 5, 1990

[54] METHOD FOR MAKING AROMATIC BISPHENOLS

[75] Inventors: Joachim Knebel, Darmstadt; Volker Kerscher, Reinheim; Werner Ude, Darmstadt-Arheilgen, all of Fed. Rep. of Germany

[73] Assignee: Röhm GmbH, Darmstadt, Fed. Rep. of Germany

[21] Appl. No.: 262,899

[22] Filed: Oct. 26, 1988

[30] Foreign Application Priority Data

Oct. 30, 1987 [DE] Fed. Rep. of Germany ....... 3736814

[51] Int. Cl.$^5$ .................... C07C 39/17; C07C 39/12; C07C 37/20
[52] U.S. Cl. .................................. 568/727; 568/722; 568/728
[58] Field of Search .................... 568/727, 728, 722

[56] References Cited

U.S. PATENT DOCUMENTS

| | | | |
|---|---|---|---|
| 4,365,099 | 12/1982 | Faler | 568/727 |
| 4,400,555 | 8/1983 | Mendiratta | 568/728 |
| 4,590,303 | 5/1985 | Mondiratta | 568/728 |

FOREIGN PATENT DOCUMENTS 0180133  5/1986  European Pat. Off. .

*Primary Examiner*—Werren B. Lone
*Attorney, Agent, or Firm*—Curtis, Morris & Safford

[57] ABSTRACT

A method for making aromatic bisphenols such as 9,9-bis-(4-hydroxyphenyl)fluorene by reacting an aromatic ketone, for example a diaryl ketone or diaryl diketone, with a phenol in the present of an insoluble strongly acidic cationic ion exchange resin as an acidic condensation catalyst, which latter may be used in the presence of a co-catalyst containing sulfur.

8 Claims, No Drawings

METHOD FOR MAKING AROMATIC BISPHENOLS

The present invention relates to a method for making an aromatic bisphenol compound by reacting a phenol with an aromatic ketone, for example for making 9,9-bis(4-hydroxyphenyl-fluorene by reacting phenol with fluorenone, in the presence of an acidic condensing agent as a catalyst.

A number of processes have been described for the preparation of 9,9-bis(4-hydroxyphenyl)fluorene, which is of interest as an intermediate particularly in the preparation of polycondensation products. In these prior art processes, the synthesis of the compound is performed by reacting fluorenone with phenol, with the cleavage of water, in the presence of an acidic condensing agent.

As is apparent from U.S. Pat. No. 4,049,721 and from European patent No. 0,065,060, 9,9-bis(4-hydroxyphenyl)fluorene can be prepared by using hydrogen chloride, introduced into the reaction mixture as a gas, as an acidic condensation catalyst. Example 1 of the U.S. patent adds β-mercapto propionic acid, whereas the European patent adds a divalent, trivalent, or tetravalent metal chloride, to the hydrogen chloride as an effective co-catalyst.

A serious drawback of working with hydrogen chloride or concentrated hydrochloric acid is the extensive corrosion these agents induce in the metal equipment used in the large scale production of products such as 9,9-bis(4-hydroxyphenyl-fluorene. The metal halides used as co-catalysts are just as corrosive as hydrogen chloride or concentrated hydrochloric acid. The corrosiveness of the HCl-containing reaction mixtures is aggravated by the water added in reprocessing. Moreover, the dilute HCl-containing aqueous solutions then obtained are difficult to work up.

U. S. Pat. No. 4,675,458 describes a process for the production of 9,9-bis(4-hydroxyphenyl)fluorene in which sulfuric acid with over 70% $H_2SO_4$ is used as an acidic condensing agent. This process overcomes the drawbacks of working with corrosive HCl-containing reaction mixtures or wash waters. The reaction mixtures containing sulfuric acid are advantageously worked up by diluting them with water, which results in dilute sulfuric acids containing also other substances, particularly excess phenol. These solutions have to be disposed of.

From Rec. Trav. Chim. 87,599 (1968) there is known the reaction of benzil, a diaryl ketone, with resorcinol in the presence of concentrated sulfuric acid as condensing agent, which gives 30.4% yields of 3,8-dihydroxy-5a, 10b-diphenylcoumarano2', 3', 2,3-coumaran, an aromatic bisphenol. This bisphenol has the formula

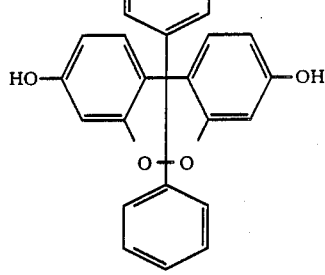

(I)

For the preparation of bis-(4-hydroxyphenyl)alkanes by condensation of phenols with aliphatic or cycloaliphatic carbonyl compounds, anhydrous, insoluble cation exchangers containing sulfonic groups are used to advantage, as described in published German patent application No. 28 11 182, German patent No. 27 22 683 and European patent No. 0 023 325, for example. This does away with the need for disposing of diluted aqueous acid solutions, and the reaction products are obtained in a purer form than in working with the acidic but water soluble condensing agents used up to now.

THE OBJECT AND THE INVENTION

The invention had as its object to find an operating procedure for reacting aromatic ketones with phenols that would permit the continued use of an acidic condensation catalyst as a genuine catalyst and thus to dispense with the continual disposal of aqueous catalyst acid.

It has been found that diaryl ketones such as fluorenone or benzil, as a diaryl ketone, will condense with phenols to form aromatic bisphenol compounds in the presence of strongly acidic cation exchangers as condensation catalysts. The acidic catalyst used in accordance with the invention cannot be dissolved out with water and theoretically is available for an infinite number of reaction steps.

The discovered reaction is surprising since in the light of the prior art cited above the use of strongly acidic cation exchangers as condensation catalysts appeared to be limited to the reaction of aliphatic and cycloaliphatic carbonyl compounds with phenols, and more particularly to the commercially important bisphenol A synthesis using acetone as the carbonyl compound.

To further increase the reaction rat in the inventive process, organosulfur compounds are used to advantage as cocatalysts in the reaction mixture. They may be added to the mixture of the reactants as free compounds or may be chemically combined with the ion-exchange resin. Suitable organosulfur compounds are, in particular, substances containing mercapto groups.

The invention thus relates to a process for producing aromatic bisphenol compounds by reacting aromatic ketones with phenols in the presence of acidic condensing agents serving as catalysts and of mercaptans serving a cocatalysts which is characterized by the use of an insoluble, strongly acidic cation exchange resin as acidic condensation catalyst.

PRACTICE OF THE INVENTION

The diaryl ketones which are preferably reacted with phenols by the process of the invention are compounds of the general formula

wherein $R_1$ and $R_2$ may be alike or different and are aromatic groups, and in particular phenyl and $C_1$–$C_4$ alkyl-substituted phenyl, $R_1$ and $R_2$ being optionally further bound together by a single bond or a $CH_2$ group, or by an oxygen or sulfur atom, and a may be 1 or 2.

Suitable ketones of formula (II) are fluorenone, anthrone, xanthone, thioxanthone, benzil, and phenanthrenequinone. Particularly well suited are the ketones fluorenone and benzil, and especially fluorenone.

The phenol to be used should be unsubstituted in a position para to the hydroxyl group but may be substituted in positions Oct. 3, 88 ortho and meta to the phenolic group with one or more $C_1$–$C_4$ alkyl groups, and in particular methyl groups, but also with further OH groups, as in resorcinol, for example.

Aromatic diketones (with a = 2 in [II]) react preferentially on only one carbonyl group in the sense of the phenol-ketone condensation. However, the second carbonyl group may enter into further reactions, as is apparent from formula (I), for example, for the reaction product of benzil with resorcinol.

The process of the invention is preferably carried out with a stoichiometric excess of phenol. However, it may also be carried out with a stoichiometric excess of diaryl ketone. A molar ratio of diaryl ketone to phenol of from 1:2 to 1:10, and more particularly from 1:3 to 1:6, is preferred.

The ion exchange resins which are suitable for use as acidic condensation catalysts include, in particular, macroporous sulfonated Oct. 3, 88 crosslinked polystyrenes or corresponding styrene/acrylate copolymers available as Lewatit ® or Amberlite ®, or poly(perfluoroalkylene)sulfonic acid, available as Nafion ®. In addition to the acidic groups, and particularly the $SO_3H$ groups, which are responsible for the protonic catalysis, groups of molecules having an SH function may be attached to the ion exchange resins, either directly to the matrix or through the sulfonic groups, as a result of which the mercaptan cocatalysis is likewise controlled from the ion exchange resin. For example, European patent No. 0 023 325 describes a polystyrene crosslinked with divinylbenzene which comprises, in addition to the sulfonic groups formed through the hydrolysis of sulfonyl chloride groups, resin regions incorporating SH groups as a result of the partial reaction with cysteamine of sulfonyl chloride groups introduced into the polymer. (See also European patent No. 0 049 411.) With regard to ion exchangers, see Ullmanns Enzyklopädie der technischen Chemie, 4th ed., vol. 13, pp. 279–280, and especially p. 313 and pp. 534–535.

However, the cocatalyst incorporating mercaptan groups may be present in the reaction also in uncombined form as a low molecular weight compound, for example, as beta-mercaptopropionic acid.

The process of the invention may be carried out continuously or batchwise. Continuous operation is preferred. In the batch process, the reactants and the catalyst are thoroughly stirred mechanically to assure better contact, and hence an improved spacetime yield. In continuous operation, the exchange resins, which generally are used in the form of tiny beads or as as irregularly shaped particles ranging in size from 0.5 to about 5 mm, are disposed as a fixed bed, for example, in a vertical, tubular reactor, with the reaction mixture flowing through the bed.

Depending on the type of compound to be produced, the reaction temperature will range from about 20° to about 150° C. Temperatures between 20° and about 100° C. are preferred.

The reaction may optionally be carried out in the presence of an inert solvent such as toluene, cyclohexane, or fluorobenzene, which during the reaction can serve as a water entrainer, if necessary.

The pressure in the reaction zone generally ranges from 0.1 to 10 bar, and more particularly from 0.5 to 3 bar.

The ion exchangers used have a total H ion capacity of from about 2.5 to about 6 meq/g of dry solids.

When the mercaptan cocatalyst is not bound to the ion exchange resin, it is added to the reactants in an amount of from 0.003 to 0.05 mole per mole of diaryl ketone to be reacted. Betamercaptopropionic acid, for example, is used as sulfur compound.

On completion of the reaction, the reaction mixture is separated from the ion exchanger by filtering, optionally after dilution with a water miscible solvent. The reaction product solution may then be concentrated by evaporation and repeatedly extracted with boiling water for the removal of excess phenol. Another effective method of separating excess phenol is its removal by steam distillation. The product so obtained may then be recrystallized for further purification.

A better understanding of the present invention and of its many advantages will be had from the following specific examples, given by way of illustration.

EXAMPLE 1

A mixture of 22.5 g (0.125 mole) of fluorenone, 58.8 g (0.625 mole) of phenol, 0.03 ml of β-mercaptopropionic acid, and 30 g of "Amberlyst 16", a macroporous, strongly acidic cationic ion exchanger (Rohm & Haas) comprising sulfonated polystyrene crosslinked with divinyl benzene and having an acid capacity of 5.0 meq/g (by dry weight), was charged under an argon atmosphere into a Witt jar equipped with a U-shaped metal stirrer and stirred at 100° C.

After 2 hours, the fluorenone had been completely reacted. (Thin layer chromatographic analysis: silica gel/acetone-cyclohexane 1:2). On cooling to room temperature, 110 ml of isopropanol were added, the mixture was heated and then separated from the ion exchanger while hot, and 110 ml of water were added to the filtrate with stirring. The cooled ion exchanger was washed three times with 100 ml portions of acetone and dried under vacuum at 60° C. The acetone solutions were mixed with an equal volume of water and combined with the isopropanol solution. The precipitated raw product was filtered off with suction, extracted three times by boiling with 250 ml portions of water, and recrystallized from 110 ml of isopropanol.

Yield: 30 g (68.5% of theory) of 9,9-bis(hydroxyphenyl)fluorene. m.p.: 221° C.

EXAMPLE 2

Example 1 was repeated using 30 g of "Lewatit SPC 118" (Bayer AG) as the catalyst. The latter is, again, an ion exchanger comprising polystyrene sulfonic acid crosslinked with divinyl benzene and having an acid capacity of 4.3 meq/g (dry weight). The reaction time was 6 hours.

Yield: 32.8 g (74% of theory). m.p.: 222°–223° C.

EXAMPLE 3

Example 1 was repeated except that the used "Amberlyst" catalyst of Example 1 was re-used. Reaction time was 6 hours.

Yield: 26.1 g (59.6% of theory) of 9,9-bis(hydroxyphenyl)-fluorene. m.p.: 222°–224° C.

EXAMPLE 4

A mixture of 20 g (0.11 mole) of fluorenone, 20.7 g (0.22 mole) of phenol, 0.03 ml of β-mercaptopropionic acid, 100 ml fluorobenzene and 5 g of "Amberlite XE Oct. 3, 88 386" (Rohm & Haas) was dissolved in a water separator with reflux un no further water separated (1.5 hours). The product precipitated during the reaction. 30 ml of isopropanol were added to the reaction mixture, which was heated and then filtered while hot, the filtrate then being evaporated to dryness. The raw product was recrystallized from isopropanol.

Yield: 29 g (75% of theory) of 9,9-bis(hydroxyphenyl)fluorene. m.p. : 224° C.

"Amberlite XE 386" is a macroporous, strongly acidic cationic ion exchanger comprising sulfonated polystyrene crosslinked with divinyl benzene and having an acid capacity of 1.95 meq/ml (moist bulk volume).

EXAMPLE 5

Example 4 was repeated except that cyclohexane was used as a water entrainer.

Yield: 25 g (65% of theory). m.p.: 224° C.

EXAMPLE 6

Example 5 was repeated using toluene as the water entrainer. The product remained in solution during the reaction. The solution was separated from the ion exchanger by filtration, the solvent (toluene) was distilled off, and the raw product was recrystallized from isopropanol.

Yield: 23 g (60% of theory) m.p.: 224° C.

EXAMPLE 7

10 g of a strongly acidic ion exchanger "A-16" (="Amberlyst 16") of Rohm & Haas was added to a solution of 20 g (95 millimoles) of benzil and 21 g (190 millimoles) of resorcinol in 120 ml of toluene and heated to reflux until no further water separated (2 hours). On cooling, the resulting reaction mixture was filtered, evaporated to dryness, extracted once by boiling with 60 ml of chloroform, and again filtered. The solid mass remaining was recrystallized from ethanol/water (2:1).

Yield: 21 g (55 millimoles; 56% of theory) of 3,8-dihydroxy-5a,10b-diphenylcoumarano-2', 3', 2,3-coumaran. m.p.: 254° C.

What is claimed is:

1. A method for making 9,9-bis(4-hydroxyphenyl)-fluorene which comprises reacting fluorenone with phenol at a temperature from 20° C. to 150° C. in the presence of an insoluble, strongly acidic cationic ion exchange resin as a condensation catalyst.

2. A method as in claim 1 performed in an inert solvent.

3. A method as in claim 1 performed in the presence of a co-catalyst which is β-mercaptopropionic acid.

4. A method as in claim 1 wherein said cationic ion exchange resin contains free mercapto groups.

5. A method for making 3,8-dihydroxy-5a,10b-diphenylcumarano-2',3',2,3cumaran which comprises reacting benzil with resorcinol at a temperature from 20° C. to 150° C. in the presence of an insoluble, strongly acidic cationic ion exchange resin as a condensation catalyst.

6. A method as in claim 5 performed in an inert solvent.

7. A method as in claim 5 performed in the presence of a co-catalyst which is β-mercaptopropionic acid.

8. A method as in claim 5 wherein said cationic ion exchange resin contains free mercapto groups.

* * * * *

UNITED STATES PATENT AND TRADEMARK OFFICE
CERTIFICATE OF CORRECTION

PATENT NO. : 4,931,594

DATED : June 5, 1990

INVENTOR(S) : Knebel et al.

It is certified that error appears in the above-identified patent and that said Letters Patent is hereby corrected as shown below:

Column 2, line 66, replace "a" by -- as --.

Column 3, line 39, delete "Oct. 3, 88".

Column 5, line 18, delete "Oct.3, 88";

line 19, replace "un" by -- until --.

Signed and Sealed this

First Day of October, 1991

Attest:

*Attesting Officer*

HARRY F. MANBECK, JR.

*Commissioner of Patents and Trademarks*